United States Patent
Chen

[11] Patent Number: 5,830,503
[45] Date of Patent: Nov. 3, 1998

[54] ENTERIC COATED DILTIAZEM ONCE-A-DAY FORMULATION

[75] Inventor: Chih-Ming Chen, Davie, Fla.

[73] Assignee: Andrx Pharmaceuticals, Inc., Fort Lauderdale, Fla.

[21] Appl. No.: 667,308

[22] Filed: Jun. 21, 1996

[51] Int. Cl.⁶ .............................. A61K 9/32; A61K 9/34; A61K 9/36; A61K 9/56
[52] U.S. Cl. .............. 424/480; 424/482; 424/481; 424/462; 424/461; 424/458; 424/457; 424/456
[58] Field of Search ........................ 424/480, 457, 424/482, 481, 458, 456, 461, 462

[56] References Cited

U.S. PATENT DOCUMENTS

| | | | |
|---|---|---|---|
| 4,839,177 | 6/1989 | Colombo et al. | 424/482 |
| 4,891,230 | 1/1990 | Geoghegan et al. | 424/461 |
| 4,894,240 | 1/1990 | Geoghegan et al. | 424/497 |
| 4,917,899 | 4/1990 | Geoghegan et al. | 424/461 |
| 4,963,365 | 10/1990 | Samejima et al. | 424/493 |
| 5,002,776 | 3/1991 | Geoghegan et al. | 424/497 |
| 5,051,262 | 9/1991 | Panoz et al. | 424/468 |
| 5,112,621 | 5/1992 | Stevens et al. | 424/497 |
| 5,137,733 | 8/1992 | Noda et al. | 424/497 |
| 5,149,542 | 9/1992 | Valducci | 424/493 |
| 5,229,135 | 7/1993 | Philippon et al. | 424/494 |
| 5,286,497 | 2/1994 | Hendrickson et al. | 424/490 |
| 5,288,505 | 2/1994 | Deboeck et al. | 424/497 |
| 5,336,504 | 8/1994 | Geoghegan et al. | 424/462 |
| 5,344,657 | 9/1994 | Desmolin | 424/458 |
| 5,364,620 | 11/1994 | Geoghegan et al. | 424/497 |
| 5,376,384 | 12/1994 | Eichel et al. | 424/480 |
| 5,419,917 | 5/1995 | Chen et al. | 424/469 |
| 5,422,123 | 6/1995 | Conte et al. | 424/479 |
| 5,472,710 | 12/1995 | Klokkers-Bethke et al. | 424/468 |
| 5,529,790 | 6/1996 | Eichel et al. | 424/480 |
| 5,578,321 | 11/1996 | Sherman | 424/453 |

FOREIGN PATENT DOCUMENTS

| | | |
|---|---|---|
| 0263083 | 4/1988 | European Pat. Off. . |
| 0282698 | 9/1988 | European Pat. Off. . |
| 0463877 | 1/1992 | European Pat. Off. . |
| 6671167 | 9/1995 | European Pat. Off. . |
| 2624732 | 12/1987 | France . |
| 8803795 | 6/1988 | WIPO . |

*Primary Examiner*—Thurman K. Page
*Assistant Examiner*—James M. Spear
*Attorney, Agent, or Firm*—Hedman, Gibson & Costigan, P.C.

[57] ABSTRACT

A once-a-day diltiazem dosage form which comprises: (a) a core element which is a compressed tablet which contains a therapeutic dose of diltiazem and an amount of a solubility modulating substance that controls the release of said diltiazem in order to provide a therapeutic level over a period of about 24 hours; and (b) on the outer surface of the core element, a sufficient amount of an enteric coating that causes the diltiazem to release at a rate that permits the use of once-a-day dosing to maintain steady state therapeutic levels of diltiazem.

10 Claims, 2 Drawing Sheets

ENTERIC COATED DILTIAZEM ONCE-A-DAY FORMULATION

BACKGROUND OF THE INVENTION

The present invention relates to controlled release unit dose formulations of diltiazem hydrochloride (diltiazem). Diltiazem is sold commercially in extended release pharmaceutical dosage forms in order to maintain a therapeutic serum level of diltiazem and to minimize the effects of missed doses of drugs caused by a lack of patient compliance. The minimum therapeutic plasma diltiazem concentrations are in the range of 50 to 200 ng/ml.

In the prior art extended release formulations of diltiazem tablets have been marketed which provide 24 hour therapeutic blood levels of diltiazem with once a day administration of a single dosage unit. These tablets are known as Dilacor XR®. This product is described as a once-a-day capsule which contains multiple units of diltiazem hydrochloride. This product is also described in U.S. Pat. No. 4,839,177 which discloses that the tablet comprises a core of diltiazem hydrochloride and a swellable polymer and a support platform applied to the tablet. The support platform is described in the text of U.S. Pat. No. 4,839,177 as being "inert and insoluble in the medium into which the active substance is to be transferred".

In U.S. Pat. No. 5,229,135, a once-a-day formulation is described that is based on a single pellet which is prepared with an active core which is coated with diltiazem and an inner and outer membrane.

Other diltiazem formulations are disclosed in U.S. Pat. Nos. 4,721,619; 4,894,240; 5,002,776; 5,364,620; 4,891,230; 4,917,899; 5,288,505; 5,470,584; 5,286,497 and U.S. Pat. No. 5,336,504.

The present invention provides a novel diltiazem once-a-day formulation which is a tablet formulation which does not have a support platform or a coating that is soluble in an aqueous medium. As used herein, the term diltiazem includes the free base form and pharmaceutically acceptable salts of diltiazem such as diltiazem hydrochloride.

SUMMARY OF THE INVENTION

The present invention is directed to a once-a-day controlled release diltiazem formulation which comprises:
  (a) a core element comprising a compressed tablet which comprises a therapeutic dose of diltiazem and an amount of a solubility modulating substance which is sufficient to control the release of said diltiazem to provide a therapeutic level over a period of about 24 hours; and
  (b) a sufficient amount of a substantially uniform enteric coating which is placed around said core element.

The present invention provides a dosage form with various release rate profiles in various pH dissolution media for diltiazem which are a substantially zero order release rates (FIG. 1). It is surprising and unexpected that the zero order in vitro release characteristics of the dosage form of the present invention provides substantially the same in vivo plasma levels of diltiazem which is provided by a commercial formulation which does not have an enteric coating (FIG. 2).

It is an object of the invention to provide a a once-a-day diltiazem dosage system.

It is also an object of the present invention to provide a once-a-day diltiazem dosage system which does not have a support platform layer.

It is also an object of this invention to provide a once-a-day diltiazem dosage system which avoids initial high plasma levels of diltiazem but maintains a therapeutic level of diltiazem with a once-a-day dosage system.

It is also an object of the present invention to provide a once-a-day diltiazem dosage system which has a substantially zero order release dissolution profile of diltiazem.

It is also an object of this invention to provide a once-a-day diltiazem dosage system which provides a diltiazem serum concentration of from 50 to 200 ng/ml.

These and other objects of the invention will become apparent from the appended specification.

DETAILED DESCRIPTION OF THE INVENTION

Figure 1:
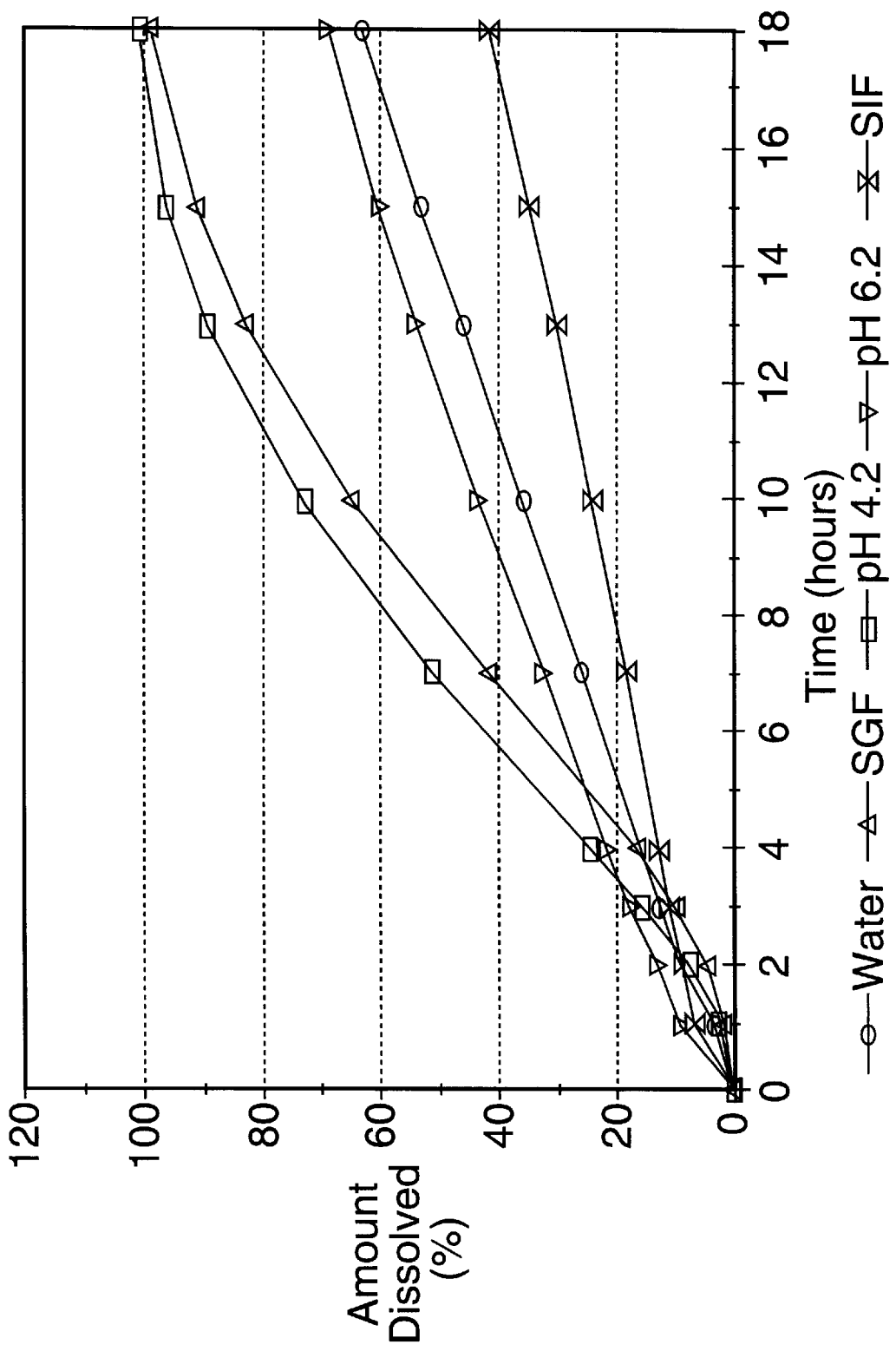
FIG. 1 is a graph of the dissolution profile of a 240 mg diltiazem capsule containing 4 diltiazem tablets made according to the Example of the present application in water, SGF, pH 4.2, pH 6.2 and SIF.
Figure 2:
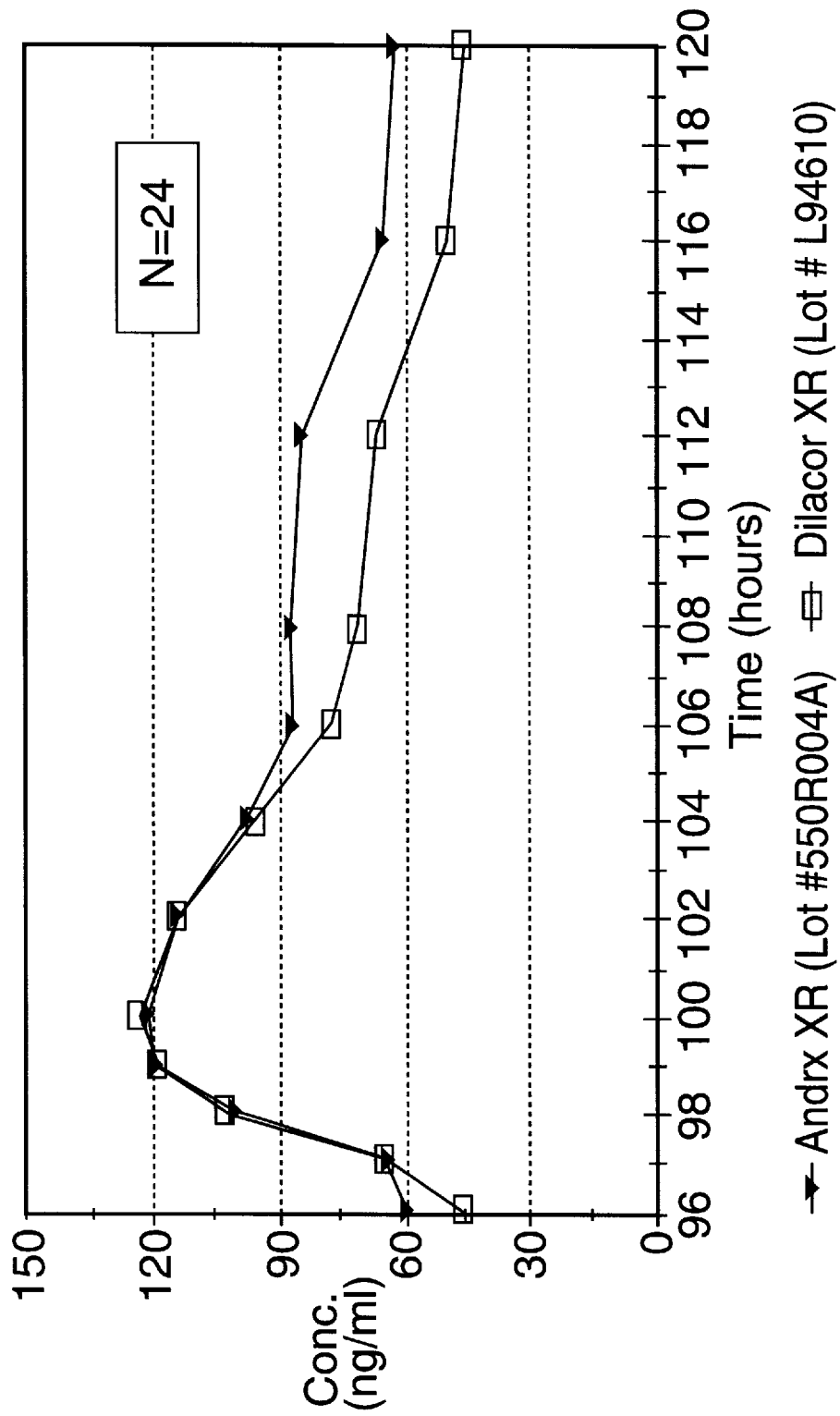
FIG. 2 is a graph of a linear plot of the steady state plasma levels that were determined in an in vivo multiple dose test of the same diltiazem capsule that was used in the test of FIG. 1 and Dilacor XR in 24 fasting healthy subjects.

The once-a-day diltiazem controlled release formulation of the invention provides an alternative to the prior art diltiazem formulations which require the presence of a support platform layer to achieve a sufficient steady state plasma level of diltiazem which permits once-a-day dosing. Diltiazem is subject to a first pass effect which gives it an absolute bioavailability of about 40% as compared to intravenous administration. This biological phenomenon must be considered in formulating a product that will provide a therapeutic plasma level of diltiazem based on once-a-day dosing.

The core element of the applicants' diltiazem dosage form comprises a compressed tablet which comprises a therapeutic dose of diltiazem and an amount of a solubility modulating substance which is sufficient to control the release of said diltiazem to provide a therapeutic level over a period of about 24 hours.

The solubility modulating substance is preferably dibasic sodium phosphate, but it is possible to use other solubility modulating agents such as sodium chloride, tribasic sodium phosphate, hydrogel forming polymers, such as hydroxypropyl methylcellulose, hydroxypropyl cellulose, hydroxyethyl cellulose, sodium alginate, xanthan gum, carbomer, and the like. In addition other pharmaceutically acceptable diluents such as lactose, dextrose, sucrose, starch, microcrystalline cellulose, dicalcium phosphate and the like.

The core element is preferably manufactured by first passing all of the dry ingredients through a screen (e.g. 300 mesh USSS) and thereafter tumble blending the dry ingredients for 5 to 120 minutes to form a compressible powder blend. The compressible powder blend is preferably pressed into tablets using an automatic tabletting machine provided with a suitable die.

The core element is coated with an enteric coating composition which in combination with the solubility modulating hydrogel provides the extended release of the diltiazem component. As used herein and in the appended claims, the term "enteric coating" is used to define a "pH dependent" coating which will resist dissolution in the acidic medium of the stomach and will dissolve in the environment of the small intestine. The enteric coating will comprise from 1 to 10% and preferably 1 to 6% and most preferably from 2 to 4% by weight based on the combined weight of the tabletted core and the coating. The enteric coating polymer may be selected from the group consisting of shellac, methacrylic acid copolymers, (Eudragit S or L) cellulose acetate phthalate, hydroxypropylmethylcellulose phthalate, hydroxypropylmethylcellulose acetate succinate, cellulose acetate trimellitate and polyvinyl acetate phthalate. The preferred polymer is hydroxypropylmethylcellulose phthalate. The thickness of the coating is selected to provide the desired release rate which is dependent on the thickness of the coating and the particular coating.

A preferred polymer is hydroxypropyl methylcellulose phthalate, NF (Type 200731) which is a monophthalic acid ester of hydroxypropyl methylcellulose. It contains not less than 18.0 percent of methoxy groups, not less than 5.0 percent and not more than 9.0 percent of hydroxypropoxy groups, and not less than 27.0 and not more than 35.0 percent of phthalyl groups, calculated on a dry basis. Other auxiliary coating aids such as a minor amount (1–5 wt. % based on the active core component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof in combination with an antisticking agent which may be a silicate such as talc. The antisticking agent may be added in an amount which is equivalent to 0.3 to 1.0:1.0 by weight of the enteric coating polymer. These components may be added to the enteric coating polymer in combination with appropriate solvents.

The enteric coated tablet core contains an active core which is coated with a sufficient amount of the enteric coating which will substantially maintain its integrity in the acidic region of the gastrointestinal tract. The enteric coated tablet is designed to release diltiazem in vitro in a substantially zero order release profile in simulated gastric fluid over a period of about 2 to 18 hours after the dosage form of the invention is placed in simulated gastric fluid.

The tablet core of the invention may comprise:

diltiazem hydrochloride, USP 20 to 40 wt. % anhydrous lactose, NF 25 to 40 wt. % hydroxypropyl methylcellulose, USP 28 to 42 wt. % dibasic sodium phosphate, USP 5 to 15 wt. % colloidal silicon dioxide 0.1 to 2 wt. % magnesium stearate, NF 1.0 to 2 wt. %

The coating suspension for a 10.5 Kg. batch of tablets may be prepared by blending:

|  | wt/percent | Kg/batch |
| --- | --- | --- |
| hydroxypropyl methyl cellulose phthalate, NF | 69.0% | 0.217 |
| hydroxypropyl cellulose, NF | 3.3% | 0.011 |
| talc, USP | 20.7% | 0.065 |
| acetyl tributyl citrate | 7.0% | 0.022 |
| isopropyl alcohol, USP | — | 4.190 |
| purified water, USP | — | 1.796 |

A sufficient amount of the isopropyl alcohol and the purified water are added to form a coating suspension. The isopropyl alcohol and the purified water are evaporated during processing and do not appear in the final product.

The controlled release diltiazem formulation of the invention will preferably have a dissolution release rate, in 900 ml of simulated gastric fluid in a USP 23 Type II apparatus at 37° C. and 100 rpm as measured by UV at 237 nm, which substantially corresponds to the following:

a) from 0 to 20 wt. % and preferably from 5 to 15 wt. % of total diltiazem is released after 3 hours;

b) from 30 to 55 wt. % and preferably from 35 to 50 wt. % total diltiazem is released after 7 hours;

c) from 55 to 80 wt. % and preferably from 60 to 75 wt. % after 10 hours;

d) not less than 70% of total diltiazem after 13 hours;

e) not less than 85% of total diltiazem is released after 18 hours.

Simulated gastric fluid consists of 2.0 g sodium chloride; 3.2 g pepsin in 7.0 ml of hydrochloric acid (37%) and sufficient water to make 1000 ml. The pH is about 1.2 The term "total diltiazem" is used to point out the measurable quantity of diltiazem that is found when UV analysis using a Beckman UV spectrophotometer at 237 nm is carried out.

The enteric coated tablets of the invention and may be placed in soft or hard gelatin capsules.

Generally the dosage form will contain from about 120 to 240 mg of diltiazem hydrochloride or its equivalent which may be prepared by placing 2 to 4 tablets, which are prepared according to the Example in a hard gelatin capsule.

DESCRIPTION OF THE PREFERRED EMBODIMENTS

EXAMPLE

A diltiazem hydrochloride core tablet was prepared having the following formulation:

|  | wt % | mg/tablet |
| --- | --- | --- |
| diltiazem hydrochloride, USP | 26.1 | 60.0 |
| anhydrous lactose, NF | 32.7 | 75.2 |
| hydroxypropyl methylcellulose, USP | 30.0 | 69.0 |
| dibasic sodium phosphate, USP | 10.0 | 23.0 |
| colloidal silicon dioxide | 0.2 | 0.5 |
| magnesium stearate, NF | 1.0 | 2.3 |
|  | 100.0 | 230 mg |

All of the ingredients except the magnesium stearate are passed through a #30 mesh (USSS) mesh screen and are blended for 10 minutes prior to adding the magnesium stearate which has been passed through a #40 mesh screen. hereafter the combined ingredients are blended for 60 minutes and compressed tablets are prepared with a Manesty Betapress using a 0.281" flat face beveled edge punch and die set.

The coating suspension was prepared at 3% coating level for a 10.5 Kg. batch by blending:

|  | wt. % | mg/tablet | Kg/batch |
| --- | --- | --- | --- |
| hydroxypropyl methyl cellulose phthalate, NF | 2.07 | 4.91 | 0.217 |
| hydroxypropyl cellulose, NF | 0.10 | 0.24 | 0.011 |
| talc, USP | 0.62 | 1.47 | 0.065 |
| acetyl tributyl citrate | 0.21 | 0.50 | 0.022 |

-continued

|  | wt. % | mg/tablet | Kg/batch |
|---|---|---|---|
| isopropyl alcohol, USP | —* | —* | 4.19 |
| purified water, USP | —* | —* | 1.796 |

*evaporates during processing

All of the ingredients of the coating suspension are dispersed in the purified water and the isopropyl alcohol.

The core tablets are coated in a pan coating apparatus (Labcoat II, O'Hara Manufacturing Ltd. to form the enteric coated tablets. A sufficient number of these 60 mg diltiazem tablets are place in a two piece gelatin capsule to form 120 mg, 180 mg or 240 mg diltiazem once-a-day dosage forms.

In a 24 healthy subjects, multiple dose study, using a formulation prepared according to the Example (four 60 mg tablets in a gelatin capsule), the following pharmacokinetic test/reference ratios were determined at 90% confidence intervals:

| Parameter | Ratio | Lower Limit | Upper Limit |
|---|---|---|---|
| AUCinterdose | 110.0 | 106.0 | 115.0 |
| Cmax | 101.0 | 94.2 | 109.0 |

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

I claim:

1. A once-a-day diltiazem dosage form which comprises:
   (a) a core element comprising a compressed tablet which comprises a therapeutic dose of diltiazem and an amount of a solubility modulating substance comprising disodium phosphate and hydroxypropyl methyl cellulose which is sufficient to control the release of said diltiazem to provide a therapeutic level over a period of about 24 hours; and
   (b) a sufficient amount of a substantially uniform enteric coating which is placed around said core element which causes the diltiazem to release at a rate that permits once-a-day dosing.

2. A once-a-day diltiazem dosage form as defined in claim 1 which includes a unit dose containment system.

3. A once-a-day controlled release diltiazem formulation as defined in claim 2 wherein the unit dose containment system consists essentially of a hard gelatin capsule.

4. A once-a-day controlled release diltiazem formulation as defined in claim 1 wherein the enteric coating polymeric material is selected from the group consisting of hydroxypropyl methylcellulose phthalate, shellac, methacrylic acid copolymers and cellulose acetate phthalate.

5. A once-a-day controlled release diltiazem formulation as defined in claim 1 wherein the enteric coating polymeric material on the core tablet contains a plasticizer.

6. A once-a-day controlled release diltiazem formulation as defined in claim 5 wherein the plasticizer is acetyltributyl citrate.

7. A once-a-day controlled release diltiazem formulation as defined in claim 4 wherein the enteric coating polymeric material is hydroxypropyl methylcellulose phthalate.

8. A once-a-day diltiazem dosage form which comprises:
   (a) a core element comprising a compressed tablet which comprises a therapeutic dose of diltiazem hydrochloride and an amount of a hydroxypropyl methylcellulose which is sufficient to control the release of said diltiazem hydrochloride to provide a therapeutic level over a period of about 24 hours; and
   (b) a sufficient amount of a substantially uniform enteric coating of hydroxypropyl methyl cellulose phthalate which is placed around said core element which causes the diltiazem hydrochloride to release at a rate that permits once-a-day dosing.

9. A once-a-day controlled release diltiazem formulation as defined in claim 1 which exhibits in simulated gastric fluid, a substantially zero order release rate which continues for about 2 hours up to about 18 hours.

10. A once-a-day controlled release diltiazem formulation as defined in claim 1 wherein the formulation has a dissolution release rate in 900 ml of simulated gastric fluid, when measured in a USP 23 apparatus, Type 2, at 37° C. and 100 rpm, measured by using UV at a wavelength of 237 nm, which substantially corresponds to the following:
   a) from 0 to 20 wt. % of total diltiazem is released after 3 hours;
   b) from 30 to 55 wt. % of total diltiazem is released after 7 hours;
   c) from 55 to 80 wt. % of total diltiazem is released after 10 hours;
   d) not less than 70% wt. % of total diltiazem is released after 13 hours;
   e) not less than 85% of total diltiazem is released after 18 hours.

\* \* \* \* \*